United States Patent
Dumitru et al.

(10) Patent No.: US 10,324,053 B2
(45) Date of Patent: Jun. 18, 2019

(54) HUMIDITY SENSORS WITH TRANSISTOR STRUCTURES AND PIEZOELECTRIC LAYER

(71) Applicant: Honeywell International Inc., Morris Plains, NJ (US)

(72) Inventors: Viorel Georgel Dumitru, Prahova (RO); Viorel Avramescu, Bucharest (RO); Octavian Buiu, Bucharest (RO); Mihai Brezeanu, Bucharest (RO); Bogdan Serban, Bucharest (RO)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/455,771

(22) Filed: Mar. 10, 2017

(65) Prior Publication Data
US 2017/0261453 A1    Sep. 14, 2017

(30) Foreign Application Priority Data

Mar. 11, 2016 (EP) .................................. 16160046

(51) Int. Cl.
*G01N 27/12* (2006.01)
*H01L 41/18* (2006.01)
(Continued)

(52) U.S. Cl.
CPC ......... *G01N 27/121* (2013.01); *G01N 27/414* (2013.01); *H01L 29/788* (2013.01);
(Continued)

(58) Field of Classification Search
CPC ... G01N 27/121; H01L 29/788; H01L 41/107; H01L 41/183
See application file for complete search history.

(56) References Cited

U.S. PATENT DOCUMENTS 4,698,657 A    10/1987  Watanabe et al.
4,728,882 A *   3/1988  Stanbro ................ G01N 27/227
                                                    204/400
(Continued)

FOREIGN PATENT DOCUMENTS

WO    2015015253 A1    2/2015

OTHER PUBLICATIONS

Hong, Hoang-Si, and Gwiy-Sang Chung. "Controllable growth of oriented ZnO nanorods using Ga-doped seed layers and surface acoustic wave humidity sensor." Sensors and Actuators B: Chemical 195 (2014): 446-451.*

(Continued)

*Primary Examiner* — Robert J Eom
(74) *Attorney, Agent, or Firm* — Craige Thompson; Thompson Patent Law

(57) ABSTRACT

An illustrative humidity sensor may include a substrate and a sensing field effect transistor. The sensing field effect transistor may comprise a source formed on the substrate, a drain formed on the substrate, a gate, and a piezoelectric layer disposed over the gate. Another illustrative humidity sensor may comprise a substrate, a semi-conductor layer disposed over the substrate, a piezoelectric layer disposed over the semi-conductor layer, a first electrode disposed on the piezoelectric layer, and a second electrode disposed on the piezoelectric layer. In some instances, the piezoelectric layer may comprise aluminum nitride.

18 Claims, 4 Drawing Sheets

(51) Int. Cl.
G01N 27/414 (2006.01)
H01L 29/788 (2006.01)
H01L 41/107 (2006.01)
H01L 41/113 (2006.01)

(52) U.S. Cl.
CPC .......... *H01L 41/107* (2013.01); *H01L 41/183* (2013.01); *H01L 41/1132* (2013.01)

(56) References Cited

U.S. PATENT DOCUMENTS

| | | |
|---|---|---|
| 5,004,700 A | 4/1991 | Webb et al. |
| 2005/0116263 A1 | 6/2005 | Lu et al. |
| 2005/0230271 A1* | 10/2005 | Levon ................ G01N 27/4145 205/789 |
| 2015/0287781 A1 | 10/2015 | Eisele |

OTHER PUBLICATIONS

Lao Chang et al., .Polymer functionalized piezoelectric-FET as humidity/chemical nanosensors; Applied Physics Letters, A I P, Publishing LLC, US, vol. 90, No. 26, Jun. 27, 2007, pp. 262107-262107.
Xudong Wang et al. Piezoelectric Field Effect Transistor and Nanoforce Sensor Based on a Single ZnO Nanowire, Nano Letters, vol. 6, No. 12, Dec. 1, 2006, pp. 2768-2772.
Europe Patent Application No. 16160046.5, Extended European Search Report, dated Sep. 9, 2016; 11 pages.
Europe Patent Application No. 16160046.5, Examination Report, dated Mar. 22, 2017; 5 pages.

\* cited by examiner

HUMIDITY SENSORS WITH TRANSISTOR STRUCTURES AND PIEZOELECTRIC LAYER

CROSS-REFERENCE TO RELATED APPLICATIONS

This application claims priority to European Patent Application No. 16160046.5 filed on Mar. 11, 2016, filed with the European Patent Office and entitled "Humidity Sensors with Transistor Structures and Piezoelectric Layer," which is incorporated herein by reference in its entirety.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

The disclosure relates generally to humidity sensors and methods for making humidity sensors.

BACKGROUND

Capacitive and resistive type humidity sensors rely on the ability of the sensing material to quickly absorb and desorb water molecules. The absorbed moisture changes the physical properties of the sensing material either by changing its resistance, permittivity, or stress, which can each directly affect the electrical response of the sensor. Bulk polyimide films are often used as the humidity sensing material in many capacitive and resistive humidity sensors. However, it may be desirable to provide alternative humidity sensors.

SUMMARY

This disclosure relates generally to humidity sensors and methods for making humidity sensors. In one example, a humidity sensor may include a substrate and a sensing field effect transistor. The sensing field effect transistor may comprise a source formed on the substrate, a drain formed on the substrate, a gate, and a piezoelectric layer disposed over the gate. In some instances, the piezoelectric layer may comprise aluminum nitride.

In another example, a humidity sensor may comprise a substrate, a semi-conductor layer disposed over the substrate, a piezoelectric layer disposed over the semi-conductor layer, a first electrode disposed on the piezoelectric layer, and a second electrode disposed on the piezoelectric layer. In some instances, the piezoelectric layer may comprise aluminum nitride.

An illustrative method of manufacturing a humidity sensor may comprise forming a sensing field effect transistor on a substrate, wherein the sensing field effect transistor comprises a source, a drain, and a gate. A piezoelectric layer may be sputtered over the gate of the sensing field effect transistor. The method may further comprise depositing a source contact electrode over the source of the sensing field effect transistor and depositing a drain contact electrode over the drain of the sensing field effect transistor.

The preceding summary is provided to facilitate an understanding of some of the features of the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following description of various illustrative embodiments of the disclosure in connection with the accompanying drawings, in which.

Figure 1A:
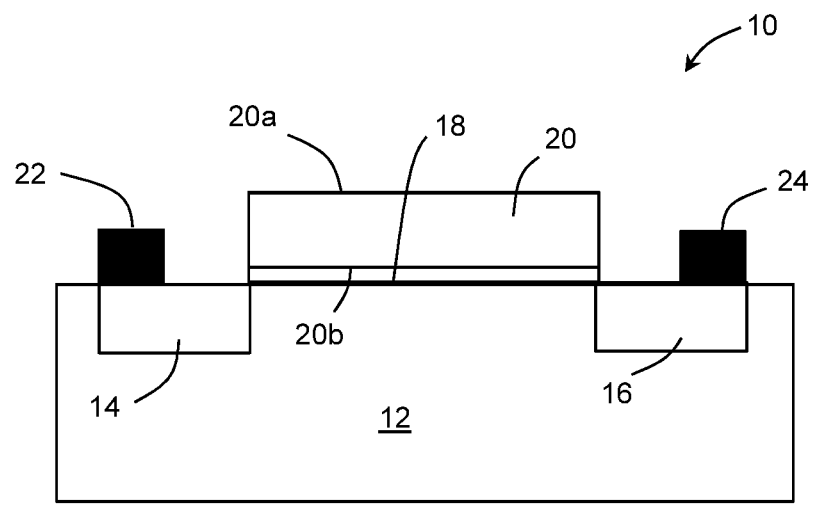
FIG. 1A is a cross-sectional view of an illustrative humidity sensor.

While the disclosure is amenable to various modifications and alternative forms, specifics thereof have been shown by way of example in the drawings and will be described in detail. It should be understood, however, that the intention is not to limit the disclosure to the particular illustrative embodiments described herein. On the contrary, the intention is to cover all modifications, equivalents, and alternatives falling within the spirit and scope of the disclosure.

DETAILED DESCRIPTION

The following description should be read with reference to the drawings wherein like reference numerals indicate like elements throughout the several views. References to "over," "under," "top," and "bottom," etc., are relative terms and are made herein with respect to the drawings and do not necessarily correspond to any particular orientation in actual physical space. The description and drawings show several examples that are meant to be illustrative of the claimed disclosure.

Humidity sensors may be used for process control in industrial applications, and for ambient air quality monitoring in homes and offices. Relative humidity (RH) sensors for cell phone and other mobile applications may become an emerging technology, within the existing trend of adding more functions to the portable applications. Most currently used humidity sensors employ either resistive (change of electrical resistance) or capacitive (change of dielectric constant) effects. The present humidity sensor may detect a change in the humidity level in the environment by a change in the current flowing through the transistor.

FIG. 1A is a diagram of an exemplary humidity sensor 10 that may be based on a field effect transistor (FET). The humidity sensor may be formed on a p-type silicon substrate or wafer 12. The sensor 10 may have an n-type source 14, an n-type drain 16, and a gate dielectric layer 18 consisting of a thermally grown thin layer of $SiO_2$ bridging n-type source 14 and n-type drain 16. As will be discussed in more detail below, a piezoelectric aluminum nitride (AlN) 20 layer may disposed over the gate 18. While the piezoelectric material is described as AlN, it is contemplated that other piezoelectric materials may also be used. The piezoelectric layer 20 may be prepared by sputter a piezoelectric material over the gate 18. The sensor 10 may further incorporate a source contact electrode 22 and a drain contact electrode 24 disposed on the substrate 12 and contacting the piezoelectric layer 20. In some instances, the contact electrodes 22, 24 may be formed from aluminum. However, this is not required. In other embodiments, the electrodes 22,24 may be formed from other electrically conductive materials such as, but not limited to platinum or gold.

The piezoelectric AlN layer 20 may have an electrical polarization that is a combination of spontaneous and piezoelectric polarization. In stationary environmental conditions, on the top side 20a of the piezoelectric layer 20, the polarization induced bound surface charge is screened by adsorbed charges from environment and charged surface defects. At the bottom side 20b of the piezoelectric layer, the polarization induced bound surface charge is compensated by charged interface defects and, eventually by charge redistribution in the semiconductor (like in HEMT transistors). Therefore, no potential difference exists between top 20a and bottom side 20b of AlN layer 20.

When humidity level changes do occur in the environment, it affects the adsorbed charge (mostly water) that compensates the polarization charge on the top surface 20a of the AlN layer 20, which is exposed to the environment. Therefore, the polarization charge will become, for a given time interval, under or overcompensated by the adsorbed charge, thus generating a net charge. On the bottom side 20b of the piezoelectric material 20 the compensating charge is not influenced by an environmental humidity change, since the water vapors cannot reach the bottom piezoelectric material surface 20b. This will lead to a potential difference between top 20a and bottom 20b side of the AlN layer 20, that will affect the current flowing through the transistor (similar to applying a gate voltage). The change in current may be correlated to the humidity of the surrounding environment.

Figure 1B:
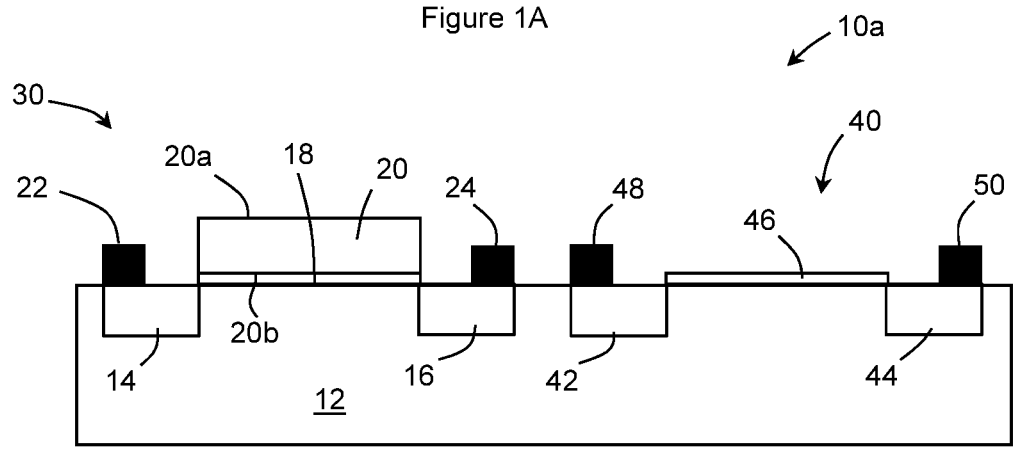
FIG. 1B is a cross-sectional view of another illustrative humidity sensor including a reference field effect transistor.

While only a sensing sensor is illustrated in FIG. 1A, it is contemplated that the humidity sensor may further include a reference sensor. In some instances, the reference sensor may be provided on a separate wafer, while in other instances the reference sensor may be provided on the same wafer as the sensing sensor. For example, FIG. 1B illustrates a humidity sensor 10a further comprising a reference FET. The humidity sensor 10a may include a sensing FET 30 including the same structure as described above with respect to FIG. 1A, where like numerals indicate like elements. The humidity sensor 10a may further include a reference FET 40. It is contemplated that the general structure of the reference sensor may be similar to the sensing sensor. However, the piezoelectric layer may be absent in the reference sensor. For example, the reference FET 40 may have an n-type source 42, an n-type drain 44, and a gate dielectric layer 46 consisting of a thermally grown thin layer of SiO$_2$ bridging n-type source 42 and n-type drain 44. The reference FET 40 may further incorporate a source contact electrode 48 and a drain contact electrode 50 disposed on the substrate 12. In some instances, the contact electrodes 48, 50 may be formed from aluminum. However, this is not required. In other embodiments, the electrodes 48, 50 may be formed from other electrically conductive materials such as, but not limited to platinum or gold.

Further, the present humidity sensor may be fabricated using various techniques. For example, phosphorus atoms may be implanted/diffused into a p-type silicon substrate to create n-doped regions forming the sources and drains of the reference and sensing FETs. A gate dielectric layer of silicon dioxide, or other appropriate gate insulator material, may then be thermally grown over the substrate followed by masking and etching to define channel regions. Growth of a thin silicon dioxide gate insulator layer, or other appropriate gate insulator material, may form the gate dielectric layer and assure a good surface state density at the silicon-silicon dioxide interface. The piezoelectric layer may then be sputtered onto the gate layer. Sputtering and patterning of an aluminum layer for contacting the source, drain, and gate electrodes may complete the fabrication of the reference and sensing FETs.

One or more of these steps may be modified if it is desirable to employ FETs implemented using different technologies, for example, n-MOS, p-MOS, CMOS, and so on. Similarly, one or more additional process steps may be employed if it is desirable to fabricate an instrumentation amplifier on the same substrate.

Figure 2:
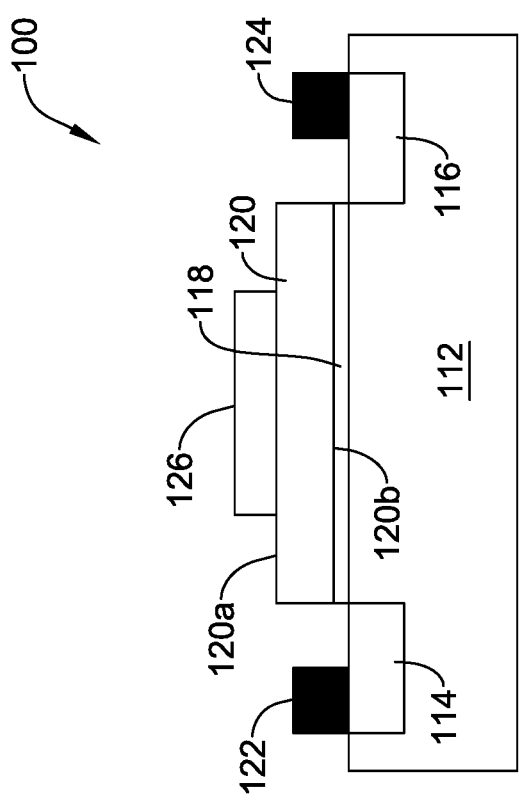
FIG. 2 is a cross-sectional view of another illustrative humidity sensor.

FIG. 2 is a diagram of another exemplary humidity sensor 100 that may be based on a field effect transistor (FET). The humidity sensor may be formed on a p-type silicon substrate 112. The sensor 100 may have an n-type source 114, an n-type drain 116, and a gate dielectric layer 118 consisting of a thermally grown thin layer of SiO$_2$ bridging n-type source 114 and n-type drain 116. As will be discussed in more detail below, a piezoelectric aluminum nitride (AlN) 120 layer may disposed over the gate 118. While the piezoelectric material is described as AlN, it is contemplated that other piezoelectric materials may also be used. The piezoelectric layer 120 may be prepared by sputter a piezoelectric material over the gate 118. The sensor 100 may further incorporate a source contact electrode 122 and a drain contact electrode 124 disposed on the substrate 112 and contacting the piezoelectric layer 120. The sensor 100 may be further provided with a gate electrode 126 disposed on the piezoelectric layer 120. In some instances, the contact electrodes 122, 124 and gate electrode 126 may be formed from aluminum. However, this is not required. In other embodiments, the electrodes 122, 124, 126 may be formed from other electrically conductive materials such as, but not limited to platinum or gold.

The piezoelectric AlN layer 120 may have an electrical polarization that is a combination of spontaneous and piezoelectric polarization. In stationary environmental conditions, on the top side 120a of the piezoelectric layer 120, the polarization induced bound surface charge is screened by adsorbed charges from environment and charged surface defects. At the bottom side 120b of the piezoelectric layer, the polarization induced bound surface charge is compensated by charged interface defects and, eventually by charge redistribution in the semiconductor (like in HEMT transistors). Therefore, no potential difference exists between top 120a and bottom side 120b of AlN layer 120.

When humidity level changes do occur in the environment, it affects the adsorbed charge (mostly water) that compensates the polarization charge on the top surface 120a of the AlN layer 120, which is exposed to the environment. Therefore, the polarization charge will become, for a given time interval, under or overcompensated by the adsorbed charge, thus generating a net charge. On the bottom side 120b of the piezoelectric material 120 the compensating charge is not influenced by an environmental humidity change, since the water vapors cannot reach the bottom piezoelectric material surface 120b. This will lead to a potential difference between top 120a and bottom 120b side of the AlN layer 120, that will affect the current flowing through the transistor (similar to applying a gate voltage). The change in current may be correlated to the humidity of the surrounding environment. While only a sensing sensor is illustrated in FIG. 2, it is contemplated that the humidity sensor may further include a reference sensor. In some instances, the reference sensor may be provided on a separate wafer, while in other instances the reference sensor may be provided on the same wafer as the sensing sensor. It is contemplated that the general structure of the reference sensor may be similar to the sensing sensor. However, the piezoelectric layer 120 may be absent in the reference sensor. It is contemplated that the humidity sensor 100 may be manufactured in a similar manner to humidity sensor 10 described above.

Figure 3:
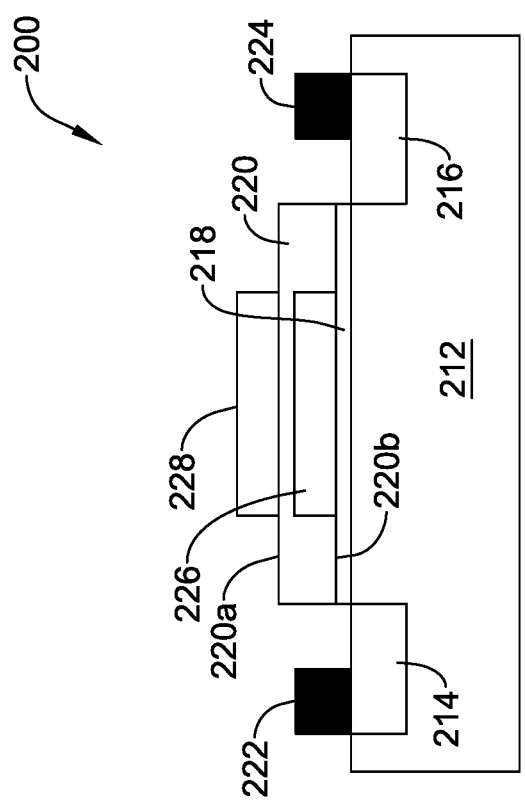
FIG. 3 is a cross-sectional view of another illustrative humidity sensor.

FIG. 3 is a diagram of another exemplary humidity sensor 200 that may be based on a field effect transistor (FET). The humidity sensor may be formed on a p-type silicon substrate 212. The sensor 200 may have an n-type source 214, an n-type drain 216, and a gate dielectric layer 218 consisting of a thermally grown thin layer of $SiO_2$ bridging n-type source 214 and n-type drain 216. As will be discussed in more detail below, a piezoelectric aluminum nitride (AlN) 220 layer may disposed over the gate 218. While the piezoelectric material is described as AlN, it is contemplated that other piezoelectric materials may also be used. The piezoelectric layer 220 may be prepared by sputter a piezoelectric material over the gate 218. The sensor 200 may further incorporate a source contact electrode 222 and a drain contact electrode 224 disposed on the substrate 212 and contacting the piezoelectric layer 220. The sensor 200 may be further provided with a gate electrode 226 disposed on the gate 218 and a supplementary electrode 228 provided on the piezoelectric layer 220. In some instances, the contact electrodes 222, 224, gate electrode 226, and supplementary electrode 228 may be formed from aluminum. However, this is not required. In other embodiments, the electrodes 222, 224, 226,228 may be formed from other electrically conductive materials such as, but not limited to platinum or gold.

The piezoelectric AlN layer 220 may have an electrical polarization that is a combination of spontaneous and piezoelectric polarization. In stationary environmental conditions, on the top side 220a of the piezoelectric layer 220, the polarization induced bound surface charge is screened by adsorbed charges from environment and charged surface defects. At the bottom side 220b of the piezoelectric layer, the polarization induced bound surface charge is compensated by charged interface defects and, eventually by charge redistribution in the semiconductor (like in HEMT transistors). Therefore, no potential difference exists between top 220a and bottom side 220b of AlN layer 220.

When humidity level changes do occur in the environment, it affects the adsorbed charge (mostly water) that compensates the polarization charge on the top surface 220a of the AlN layer 220, which is exposed to the environment. Therefore, the polarization charge will become, for a given time interval, under or overcompensated by the adsorbed charge, thus generating a net charge. On the bottom side 220b of the piezoelectric material 220 the compensating charge is not influenced by an environmental humidity change, since the water vapors cannot reach the bottom piezoelectric material surface 220b. This will lead to a potential difference between top 220a and bottom 220b side of the AlN layer 220, that will affect the current flowing through the transistor (similar to applying a gate voltage). The change in current may be correlated to the humidity of the surrounding environment. While only a sensing sensor is illustrated in FIG. 3, it is contemplated that the humidity sensor may further include a reference sensor. In some instances, the reference sensor may be provided on a separate wafer, while in other instances the reference sensor may be provided on the same wafer as the sensing sensor. It is contemplated that the general structure of the reference sensor may be similar to the sensing sensor. However, the piezoelectric layer 220 may be absent in the reference sensor. It is contemplated that the humidity sensor 200 may be manufactured in a similar manner to humidity sensor 10 described above.

FIGS. 1-3 illustrate just some potential configurations of the piezoelectric layer 20, 120, 220 used in combination with a field effect transistor. These structures are not intended to be limiting. It is contemplated that the piezoelectric layer 20, 120, 220 may be used in combination with any know FET, or other transistor technology.

Figure 4:
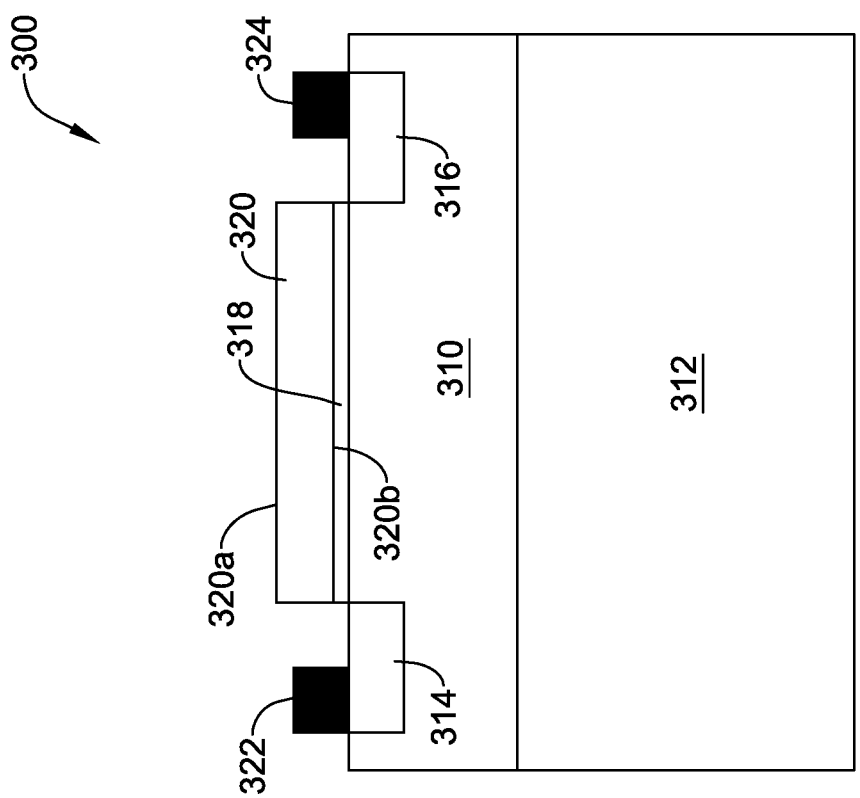
FIG. 4 is a cross-sectional view of another illustrative humidity sensor.

FIG. 4 a diagram of another exemplary humidity sensor 300 that may be based on a thin film transistor. The humidity sensor may be formed on any of the known thin film transistors, such as, but not limited to those based on amorphous or polycrystalline Si, ZnO, IGZO, ZTO, InN, AlInN, organic materials, OFET, nanowires, nanotubes, etc. Depending on the thin film technology employed, the sensor 300 may be formed on a rigid or flexible substrate 312. A semi-conductor layer 318 may be disposed over the substrate 312. As will be discussed in more detail below, a piezoelectric aluminum nitride (AlN) 320 layer may disposed over the semi-conductor layer 318. While the piezoelectric material is described as AlN, it is contemplated that other piezoelectric materials may also be used. The piezoelectric layer 320 may be prepared by sputter a piezoelectric material over the semi-conductor layer 318. The sensor 300 may further incorporate a first contact electrode 322 and a second contact electrode 324. It is contemplated that the electrodes 322, 324 may be in contact with only a portion of the piezoelectric layer. In some instances, the contact electrodes 322, 324 may be formed from aluminum. However, this is not required. In other embodiments, the electrodes 322, 324 may be formed from other electrically conductive materials such as, but not limited to platinum or gold.

The piezoelectric AlN layer 320 may have an electrical polarization that is a combination of spontaneous and piezoelectric polarization. In stationary environmental conditions, on the top side 320a of the piezoelectric layer 320, the polarization induced bound surface charge is screened by adsorbed charges from environment and charged surface defects. At the bottom side 320b of the piezoelectric layer, the polarization induced bound surface charge is compensated by charged interface defects and, eventually by charge redistribution in the semiconductor (like in HEMT transistors). Therefore, no potential difference exists between top 320a and bottom side 320b of AlN layer 320.

When humidity level changes do occur in the environment, it affects the adsorbed charge (mostly water) that compensates the polarization charge on the top surface 320a of the AlN layer 320, which is exposed to the environment. Therefore, the polarization charge will become, for a given time interval, under or overcompensated by the adsorbed charge, thus generating a net charge. On the bottom side 320b of the piezoelectric material 320 the compensating charge is not influenced by an environmental humidity change, since the water vapors cannot reach the bottom piezoelectric material surface 320b. This will lead to a potential difference between top 320a and bottom 320b side of the AlN layer 320, that will affect the current flowing through the transistor (similar to applying a gate voltage). The change in current may be correlated to the humidity of the surrounding environment. While only a sensing sensor is illustrated in FIG. 4, it is contemplated that the humidity sensor may further include a reference sensor. In some instances, the reference sensor may be provided on a separate wafer, while in other instances the reference sensor may be provided on the same wafer as the sensing sensor. It is contemplated that the general structure of the reference sensor may be similar to the sensing sensor. However, the piezoelectric layer 320 may be absent in the reference sensor.

The disclosure should not be considered limited to the particular examples described above. Various modifications, equivalent processes, as well as numerous structures to which the disclosure can be applicable will be readily apparent to those of skill in the art upon review of the instant specification.

What is claimed is:

1. A humidity sensor for sensing humidity in an environment, the humidity sensor comprising:
   a substrate;
   a sensing field effect transistor comprising:
   a source in the substrate;
   a drain in the substrate spaced from the source;
   a piezoelectric layer exposed to the environment;
   an electrical insulator situated between the piezoelectric layer and the substrate, the electrical insulator and the piezoelectric layer situated between the source and drain; and
   a gate electrode situated between the piezoelectric layer and the electrical insulator, wherein the gate is situated between the source and the drain;
   wherein the gate electrode is configured to receive a gate voltage sufficient to create the conduction channel in the substrate between the source and the drain and bias the field effect transistor into its linear region,
   wherein the piezoelectric layer is configured to generate a net charge across the piezoelectric layer in response to a change in humidity in the environment,
   wherein the change in the net charge on the piezoelectric layer is configured to modulate the conduction channel in the substrate between the source and the drain, and
   wherein a cross section of the sensing field effect transistor has the gate electrode being completely cross-sectionally enclosed by the piezoelectric layer and the electrical insulator.

2. The humidity sensor of claim 1, wherein the piezoelectric layer comprises aluminum nitride (AlN).

3. The humidity sensor of claim 2, wherein the AlN is sputtered onto the electrical insulator.

4. The humidity sensor of claim 1, further comprising a gate electrode situated above the piezoelectric layer and a source contact electrode disposed on the substrate.

5. The humidity sensor of claim 1, wherein the gate electrode situated between the piezoelectric layer and the electrical insulator is a floating gate electrode.

6. The humidity sensor of claim 1, further comprising a first gate electrode situated above the piezoelectric layer.

7. The humidity sensor of claim 1, wherein the substrate comprises a wafer, and the source corresponds to a first implant region in the substrate and the drain corresponds to a second implant region in the substrate.

8. The humidity sensor of claim 1, wherein the substrate comprises a rigid substrate.

9. The humidity sensor of claim 1, wherein the substrate comprises a flexible substrate.

10. The humidity sensor of claim 1, wherein the sensing field effect transistor comprises:
    a gate, wherein the gate comprises:
    the electrical insulator, wherein the electrical insulator is a gate oxide layer, and
    the gate electrode; and
    the piezoelectric layer situated above the gate oxide layer.

11. The humidity sensor of claim 1, wherein a bottom side of the piezoelectric layer is shielded from the environment.

12. The humidity sensor of claim 1, wherein piezoelectric layer is configured to generate the net charge for a given time interval in response to a change in an adsorbed charge on a top surface of the piezoelectric layer.

13. The humidity sensor of claim 1, further comprising a reference sensor, where the reference sensor comprises:
    a second source;
    a second drain spaced from the source; and
    a second electrical insulator situated over the substrate between the second source and the second drain.

14. The humidity sensor of claim 13, where the reference sensor does not have a piezoelectric layer.

15. A method for sensing humidity in an environment, the method comprising:
    exposing a piezoelectric layer of a humidity sensor to the environment, wherein the humidity sensor comprises:
    a substrate;
    a sensing field effect transistor comprising:
    a source in the substrate;
    a drain in the substrate spaced from the source;
    the piezoelectric layer exposed to the environment;
    an electrical insulator situated between the piezoelectric layer and the substrate, the electrical insulator and the piezoelectric layer situated between the source and drain; and
    a gate electrode situated between the piezoelectric layer and the electric insulator, wherein the gate electrode is situated between the source and the drain; and
    changing an absorbed charge on the piezoelectric layer based on a humidity in the environment;
    generate a net charge across the piezoelectric layer in response to the change in the humidity in the environment;
    modulating a conduction channel in the substrate between the source and the drain in response to the net charge on the piezoelectric layer; and
    generating a current flow through the substrate in response to the modulation of the conduction channel, wherein the current flow is indicative of the humidity in the environment,
    wherein a cross section of the sensing field effect transistor has the gate electrode being completely cross-sectionally enclosed by the piezoelectric layer and the electrical insulator.

16. The method of claim 15, wherein the humidity sensor further comprises:
    providing a gate voltage to the gate electrode sufficient to create the conduction channel in the substrate between the source and the drain and bias the field effect transistor into its linear region.

17. The method of claim 15, wherein the piezoelectric layer comprises aluminum nitride (AlN).

18. The method of claim 15, wherein a bottom side of the piezoelectric layer is shielded from the environment.

* * * * *